(12) United States Patent
Rindal et al.

(10) Patent No.: US 11,335,449 B2
(45) Date of Patent: May 17, 2022

(54) MOVEMENT STATION FOR INTERACTIVE HEALTH THERAPY

(71) Applicant: Vimocity LLC, Seattle, WA (US)

(72) Inventors: Dana Rindal, Seattle, WA (US); Kevin Rindal, Seattle, WA (US)

(73) Assignee: Vimocity LLC, Seattle, WA (US)

( * ) Notice: Subject to any disclaimer, the term of this patent is extended or adjusted under 35 U.S.C. 154(b) by 426 days.

(21) Appl. No.: 16/428,779

(22) Filed: May 31, 2019

(65) Prior Publication Data

US 2019/0371449 A1 Dec. 5, 2019

Related U.S. Application Data

(60) Provisional application No. 62/678,967, filed on May 31, 2018.

(51) Int. Cl.
*G06F 3/048* (2013.01)
*G16H 20/30* (2018.01)
*G06F 9/451* (2018.01)

(52) U.S. Cl.
CPC ............. *G16H 20/30* (2018.01); *G06F 9/451* (2018.02)

(58) Field of Classification Search
CPC .................................................... G16H 20/30
See application file for complete search history.

(56) References Cited

U.S. PATENT DOCUMENTS

| 10,932,872 | B2 * | 3/2021 | Shelton, IV | ........... G16H 40/00 |
|---|---|---|---|---|
| 11,044,221 | B2 * | 6/2021 | Shah | ....................... H04L 51/32 |
| 11,123,070 | B2 * | 9/2021 | Shelton, IV | ....... A61B 17/1227 |
| 2018/0204636 | A1 * | 7/2018 | Edwards | ................ G16H 40/67 |
| 2019/0201144 | A1 * | 7/2019 | Shelton, IV | ........... A61B 34/76 |
| 2019/0245825 | A1 * | 8/2019 | Shah | ....................... H04L 51/32 |
| 2019/0371449 | A1 * | 12/2019 | Rindal | .................. G16H 20/30 |
| 2021/0294287 | A1 * | 9/2021 | Valin | ................... G05B 19/042 |

* cited by examiner

*Primary Examiner* — David Phantana-angkool
(74) *Attorney, Agent, or Firm* — Seed IP Law Group LLP (57) ABSTRACT

Systems, methods, and devices for interactive workplace health therapy are disclosed, which include a movement station having a processor, memory, a user interface communicatively coupled to the processor, a communication interface, and at least one sensor. At least one piece of health therapy equipment is provided in a receptacle of the movement station. The sensor of the movement station is arranged to detect a mobile computing device that is in proximity of the movement station, and a user associated with the mobile computing device is identified. Based on the identity of the user, user profile information is retrieved from a user profile database. At least one directive is presented to the identified user via the user interface. The directive instructs the user in the use of the at least one piece of health therapy equipment. Information regarding the user's use of the at least one piece of health therapy equipment is collected and stored in the user profile database.

21 Claims, 6 Drawing Sheets

Fig. 5

MOVEMENT STATION FOR INTERACTIVE HEALTH THERAPY

BACKGROUND

Technical Field

The present disclosure is directed toward a movement station that, when used, will improve the health of users that interact with the movement station. More particularly, but not exclusively, the present disclosure is directed toward a movement station arranged to provide health and wellness exercise equipment and a corresponding connected computer application that delivers personalized fitness information and therapeutic exercise guidance.

Description of the Related Art

Research demonstrates that back pain, neck pain, hip pain, knee pain, shoulder pain, headaches, and other forms of pain and discomfort are all significant contributors to reduced workplace productivity. Other studies have shown that increased sitting, lack of physical activity, and poor sleep practices also contribute to reduced productivity. In many cases, the reduced productivity is associated with musculoskeletal (MSK) pain, which is not so severe that employees stay home from work, but sufficiently severe as to keep the employees from performing at full capacity.

To counter some of the ill-effects of MSK, employees may provide, or be provided with, ergonomic workstations, back support devices, foot stools, stress-relief "squeeze" toys, and other such contraptions.

All of the subject matter discussed in the Background section is not necessarily prior art and should not be assumed to be prior art merely as a result of its discussion in the Background section. Along these lines, any recognition of problems in the prior art discussed in the Background section or associated with such subject matter should not be treated as prior art unless expressly stated to be prior art. Instead, the discussion of any subject matter in the Background section should be treated as part of the inventor's approach to the particular problem, which, in and of itself, may also be inventive.

BRIEF SUMMARY

It has been recognized by the inventors that when employees are energized and enthusiastic, both the employees and the company will benefit. Productivity, efficiency, and workplace satisfaction all tend to increase. With these benefits in mind, the present inventors have created a system that helps promote healthy movement and well-being within the workplace. The system implements an evidence-guided approach used by world-class athletes to prevent injuries and improve performance. Using the systems, devices, and methods described in the present disclosure, workplace personnel are empowered to take steps that improve their movement health, physical safety, and work-life satisfaction.

An interactive health therapy system may be summarized as including: a plurality of health therapy devices; and a movement station having: a plurality of health therapy device storage areas arranged to store the plurality of health therapy devices; a memory; a processor coupled to the memory and arranged to administer a plurality of personalized movement health programs via processor-executable instructions stored in the memory; a user interface communicatively coupled to the processor and arranged to interact with a plurality of users associated, respectively, with the plurality of personalized movement health programs; a communication interface; and at least one sensor, wherein some of the processor-executable instructions, when executed, cause the processor to: communicate with a first user of the plurality of users via information passed through the communication interface to a mobile computing device associated with the first user, said information encouraging the first user to remove a selected health therapy device of the plurality of health therapy devices from the movement station; detect the removal of the selected health therapy device via data from the at least one sensor; detect the subsequent return of the selected health therapy device via data from the at least one sensor; and update a first user movement health program of the plurality of personalized movement health programs with data based on detecting the removal and subsequent return of the selected health therapy device, said first user movement health program associated with the first user.

The plurality of health therapy devices may include one or more of a massage roller, a massage ball, an arm roller, a massage cane, a step box, an acupressure device, a squeeze device, an electronic pulse massager, a heating pad, and a bolster. The plurality of health therapy device storage areas may include a plurality of receptacles integrated into the movement station. The plurality of health therapy device storage areas may include a plurality of attachment points arranged on an external surface of the movement station. In some cases, the data used to update the first user movement health program is retrieved by the movement station from the selected health therapy device.

The selected health therapy device may have at least one integrated sensor arranged to generate the data when the selected health therapy device is in use. The data generated by the at least one integrated sensor of the selected health therapy device may be data associated with at least one of: repetitions of use of the selected health therapy device, orientation of the selected health therapy device during use, and force applied to at least a portion of the selected health therapy device. In some cases, updating the first user movement health program with the data may include causing the first user movement health program to provide to the first user second information encouraging the first user to remove a different health therapy device of the plurality of health therapy devices from the movement station. In some cases, some of the processor-executable instructions, when executed, further cause the processor to accept user input data from the first user that identifies preferences of the first user; and generate predicted movement activities of interest for the first user based on the identified preferences of the first user. The predicted movement activities of interest for the first user may include at least one video game presented via the user interface of the movement station or the mobile computing device associated with the first user that requires performance of at least one health-related activity.

An interactive health therapy method may be summarized as including the acts of: determining that a known user is in proximity to a movement station, the movement station having a plurality of receptacles to store a plurality of health therapy devices; based on an identity of the known user and a personalized movement health program associated with the known user, communicating information to the known user via a communication interface, the information recommending usage of a certain type of health therapy device; detecting, via first sensor data generated by a first sensor associated with the movement station, removal of a selected health therapy device of the certain type from the movement station; subsequent to detecting the removal of the selected health therapy device, detecting, via second sensor data generated by a second sensor associated with the movement station, replacement of the selected health therapy device at the movement station; and updating movement information in the personalized movement health program associated with the known user.

The first sensor and the second sensor are in some cases the same sensor. Updating movement information in the personalized movement health program may include: capturing data generated by at least one sensor associated with the selected health therapy device; and accepting user input data, said user input data manually provided and associated with usage of the selected health therapy device. In some cases, updating movement information in the personalized movement health program includes capturing data generated by at least one sensor associated with the selected health therapy device. And in some cases, the interactive health therapy method may further include communicating second information to the known user via the communication interface, the second information recommending usage of a second certain type of health therapy device, said second certain type of health therapy device selected based on the updated movement information.

A non-transitory computer-readable storage medium may have stored contents that configure a computing system to perform a method of interactive workplace health therapy, and the method may include: providing a movement station, the movement station having a memory arranged to store data and a plurality of processor-executable software instructions, a processor coupled to the memory an arranged to execute at least some of the plurality of processor-executable software instructions, a user interface communicatively coupled to the processor, a communication interface, and at least one sensor arranged to detect a mobile computing device; providing at least one piece of health therapy equipment in a receptacle of the movement station; detecting the mobile computing device with the sensor of the movement station when the mobile computing device is in proximity of the movement station; identifying a user associated with the mobile computing device; based on the identity of the user, retrieving user profile information from a user profile database; presenting at least one directive to the identified user via the user interface, the directive instructing the user in the use of the at least one piece of health therapy equipment; collecting information regarding the user's use of the at least one piece of health therapy equipment; and storing the collected information in the user profile database.

In some cases, the receptacle of the movement station is a recessed receptacle and at least some portion of the recessed receptacle is sized and shaped to match a determined piece of health therapy equipment. In some cases, the user profile database is hosted by a remote computing server. In some cases, presenting the at least one directive to the identified user includes presenting the at least one directive via the user interface of the movement station. And in some cases, presenting the at least one directive to the identified user includes presenting the at least one directive via the mobile computing device.

This Brief Summary has been provided to introduce certain concepts in a simplified form that are further described in detail below in the Detailed Description. Except where otherwise expressly stated, the Brief Summary does not identify key or essential features of the claimed subject matter, nor is it intended to limit the scope of the claimed subject matter.

BRIEF DESCRIPTION OF THE SEVERAL VIEWS OF THE DRAWINGS

Non-limiting and non-exhaustive embodiments are described with reference to the following drawings, wherein like labels refer to like parts throughout the various views unless otherwise specified. The sizes and relative positions of elements in the drawings are not necessarily drawn to scale. For example, the shapes of various elements are selected, enlarged, and positioned to improve drawing legibility. The particular shapes of the elements as drawn have been selected for ease of recognition in the drawings. One or more embodiments are described hereinafter with reference to the accompanying drawings in which.

DETAILED DESCRIPTION

The present invention may be understood more readily by reference to this detailed description of the invention. The terminology used herein is for the purpose of describing specific embodiments only and is not limiting to the claims unless a court or accepted body of competent jurisdiction determines that such terminology is limiting. Unless specifically defined herein, the terminology used herein is to be given its traditional meaning as known in the relevant art.

In the following description, certain specific details are set forth in order to provide a thorough understanding of various disclosed embodiments. However, one skilled in the relevant art will recognize that embodiments may be practiced without one or more of these specific details, or with other methods, components, materials, etc. In other instances, well-known structures associated with fixed and mobile computing systems, including client and server computing systems as well as networks, have not been shown or described in detail to avoid unnecessarily obscuring descriptions of the embodiments.

In the present disclosure, systems, devices, and methods are disclosed that improve employee morale, energy, and retention. The inventors have recognized that many employees (e.g., who may conventionally be referred to as "manual laborers," "desk jockeys," "road warriors," and any other such terms), and office employees in particular, often work long hours in front of a computer or other equipment (e.g., industrial machines, operational controls of vehicles such as heavy equipment (e.g., bulldozers, cranes, forklifts and other heavy equipment), cars, trucks, trains, aircraft, watercraft, and others), which causes musculoskeletal (MSK) discomfort or other musculoskeletal disorders (MSDs). The MSK discomfort may include strains, sprains, muscular stress, muscular tightness, muscular fatigue, muscular atrophy, repetitive stress, general fatigue, weakness, sedentariness syndrome, dysmobility effects, reduced energy, and other such maladies. MSK discomfort is known to reduce employee happiness and employee retention in the workplace. Using the systems, devices, and methods (i.e., the teaching) of the present disclosure, healthy, individualized movement therapies and other health-centric therapies are introduced into the workplace, which reduces MSK discomfort of individual employees.

These systems, devices, and methods can be instigated in any office location anywhere, and also in non-office environments such as factories, warehouses, precincts, barracks, retail establishments, and many other environments where people work. Both standardized and customized programs can be implemented in a regimen that meets the determined needs of the particular employer and employees. For example, one or more programs can be instituted and made available to some or all users of the movement stations that are arranged according to the teaching described herein. In other cases, one or more certain programs can be selected and instituted for individual users. In these or still other cases, individual and unique programs can be instituted to meet the determined needs of a single user. The programs can be manually created, remotely created, interactively created, or created using machine learning tools. In many cases, the movement stations that are arranged according to the systems, devices, and methods described herein include tools and movement (e.g., exercise) that includes breathing, muscular rolling, stretching, balancing, dynamic tension, and other such measures.

An embodiment of the present invention includes a movement station that is desirably located in a workplace. The movement station may be a free-standing unit, a wall unit, or a movement station component integrated into a piece of furniture or real property structure.

The movement station includes one or more health-related devices; any or all of which may optionally include sensor structures or other such computing peripherals. The movement station includes a computing device having at least one network-capable transceiver. Using the computing device, the movement station is arranged to identify individual users (e.g., via a computing device associated with the user, via the user directly interacting with the movement station, or in other ways). After identification of the user, the movement station is arranged to interactively guide the user through a selected health program, which may optionally include guided stretching, breathing, movement, exercise, or other health therapy. In this way, the user is provided with education and instructions that give the user tools to decrease stiffness, soreness, or other undesirable physical manifestations related to his or her body. In at least some cases, the sensors associated with certain health-related devices, and additionally or alternatively the movement station, are able to track the usage of the particular device (e.g., weight, resistance, orientation, repetitions, speed, and other such characteristic usage data) and couple such usage to the particular user. The usage data may be used to provide encouragement, accountability, predictions of success, predictions of health-related issues, and the like to the user.

In some optional cases, the movement station may include machine learning logic. In these cases, the machine learning logic is arranged to analyze input data associated with a specific user, generate one or more determinations about the user (e.g., general health, specific malady, fatigue, sleep patterns, breathing patterns, strength, body shape, body style, and many other determinations), and individualize a health therapy regimen specifically for the specific user.

Figure 1A:
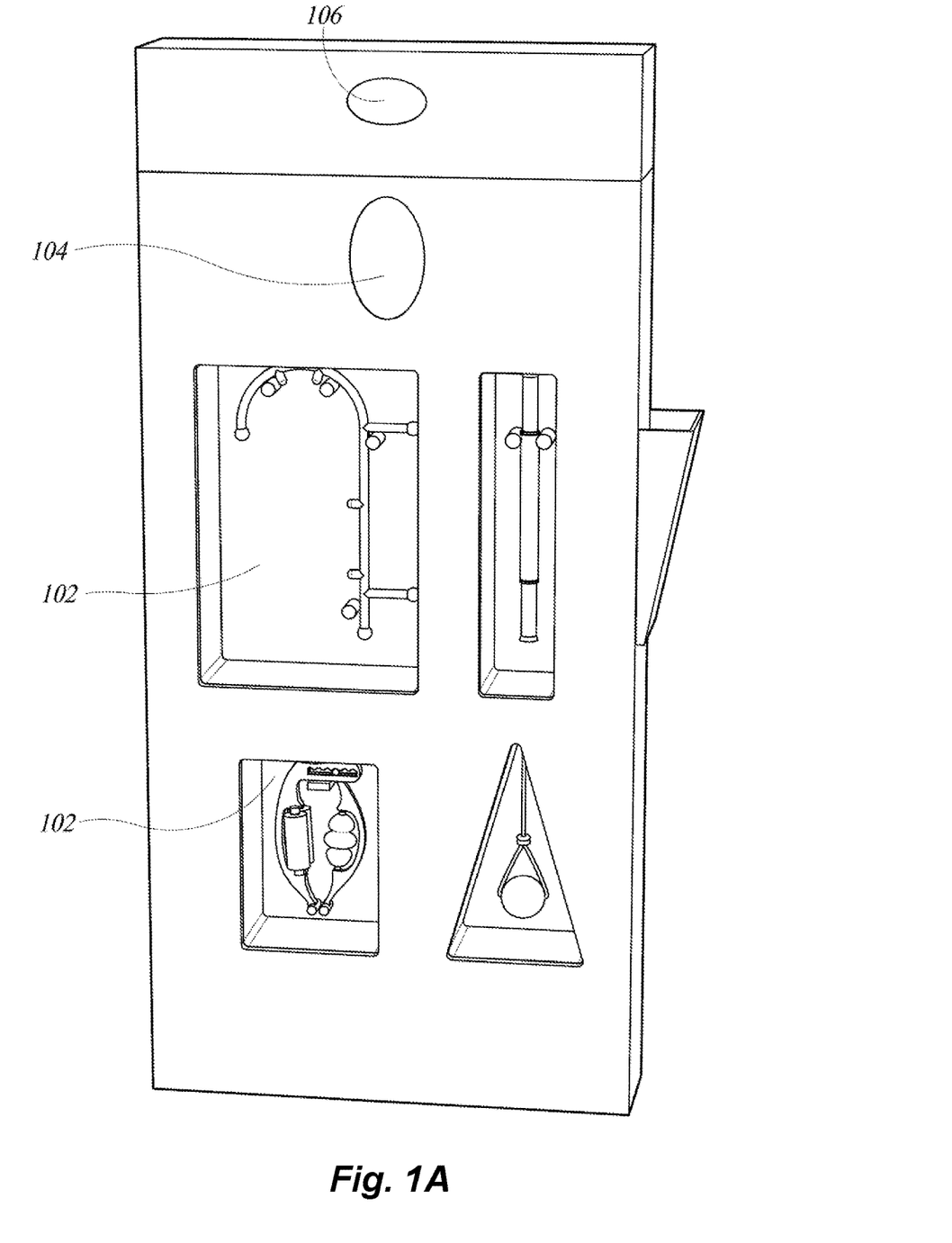
FIG. 1A is a movement station embodiment for interactive health therapy.
Figure 1B:
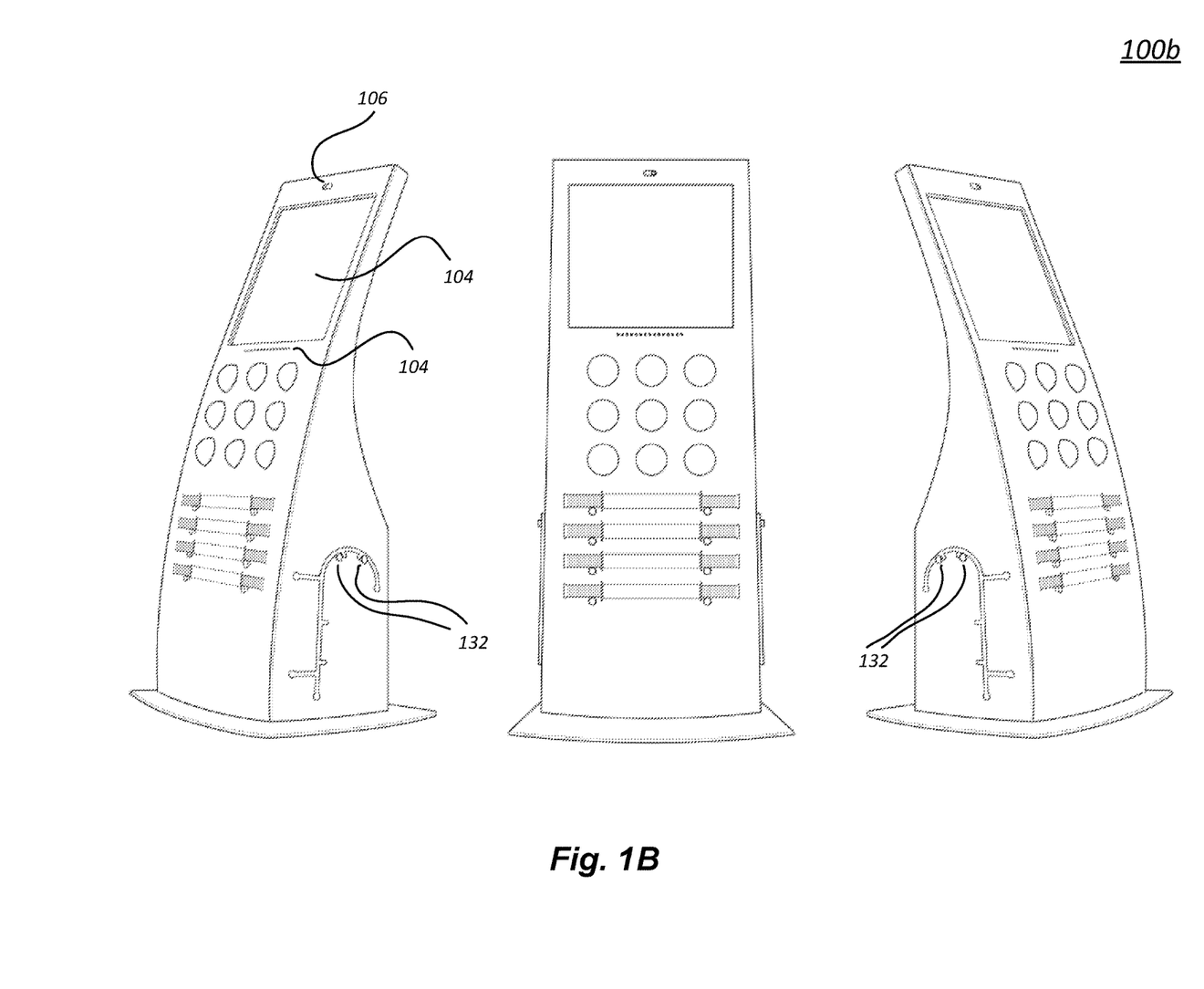
FIG. 1B is another movement station embodiment for interactive health therapy.

FIG. 1A is a movement station 100a embodiment for interactive health therapy. FIG. 1B is another movement station 100b embodiment for interactive health therapy. Collectively, FIGS. 1A and 1B may be referred to herein as FIG. 1. Collectively, except where expressly distinguished, the movement station 100a of FIG. 1A and the movement station 100b of FIG. 1B may be referred to as movement station 100. This shorthand nomenclature is provided to avoid obscuring the relevant subject matter of the present disclosure.

The movement station 100 may be a free standing unit, a mobile unit, a fixture, or the movement station 100 may be configured as some other movement station. The movement station 100 may be temporarily or permanently affixed to a wall. The movement station 100 may be a closed unit or an open shelf unit. When so configured as a closed unit, the movement station 100 may be aesthetically arranged to complement its surroundings (e.g., color, texture, size, materials, and the like). The movement station 100 may be arranged to be at least two times taller than its width. In this configuration, the movement station 100 is arranged to be addressed by a standing user rather than a sitting or bending user. Such arrangement tends to promote motion and other usefulness characteristics of the movement station 100.

A movement station 100, such as the movement station 100a of FIG. 1A, may optionally include one or more receptacles such as recessed compartments 102. Alternatively, or in addition, a movement station 100 may optionally include one or more receptacles such as attachment points 132. In FIG. 1A, four receptacles (i.e., four recessed compartments) are illustrated; only two of which are identified with reference numbers. The recessed compartments 102 or other receptacles may have common or different dimensions, shapes, or other characteristics. In some cases, the recessed compartments 102 or other receptacles are similarly configured to provide adaptable use.

In some cases, the receptacles (i.e., the recessed compartments 102 and attachment points 132 of FIG. 1) are differently configured to store specific health therapy equipment. For example, by configuring a recessed compartment 102 or attachment points 132 with a specific size, shape, orientation, and the like that matches a certain piece of health therapy equipment (e.g., a massage cane, a massage roller, an arm roller, a massage ball, or some other equipment), a user of the movement station 100 may intuitively know where to return the piece of health therapy equipment.

In some cases, recessed compartments 102, attachment points 132, and other receptacles may include one or more electronic sensors. The electronic sensors may include motion detectors (e.g., an accelerometer, microelectromechanical system (MEMs) device, infrared sensors, ultrasound sensors, radio frequency identifier (RFID) sensors, image sensors, or the like), which can be used as inventory control devices. The electronic sensors may include cameras, audio input devices, audio output devices, or any other such sensors. In some cases, a sensor in a recessed compartment 102 or a sensor coupled to an attachment point 132 or some other receptacle may communicatively couple to a sensor attached or otherwise integrated with the health therapy equipment (e.g., electronic circuitry 140, FIG. 3). Individually or collectively, the sensors of the movement station 100 and health therapy equipment may provide Internet of Things (IoT) capabilities, which permit remote detection, monitoring, control, or other network-based functions in association with the movement station 100 or its devices.

The movement station 100 of FIG. 1 includes at least one user interface 104 and at least one communication interface 106. The user interface 104 may include an output interface (e.g., display, light source, speaker, tone generator, vibrator, or the like), an input interface (e.g., keyboard, mouse, touch screen, or the like). In some cases, the user interface 104 may be configured as a tablet computing device, a mobile computing device, or some other computing device.

The communication interface 106 may include any one or more of an infrared sensor or other proximity sensing device, a plurality of light sources, a plurality of light detection sensors, a camera device, a Lidar device, an RF device (e.g., WiFi, Bluetooth, or the like). The communication interface 106 may detect the presence of a moving object or the communication interface 106 may distinguish between a human being and a non-human being. Such distinguishing may be implemented, for example, by passing image data to a remote computing device that is arranged to execute a machine vision program and return a binary (e.g., human or non-human) result. In still other cases, the communication interface 106 may identify a specific human being and distinguish one human being from another. Sometimes, the identification is made by passing image data to a remote computing device that is arranged to execute a machine vision program and return an identifier to a specific human being if such identification is made by the machine vision program. Such identification may be further facilitated by previous induction of the particular persons image into the system and agreement of the person to permit the movement station 100 to perform the image recognition. In these and in other cases, the communication interface 106 may communicate with a mobile computing device associated with a particular human being (e.g., user).

In some cases, the communication device 106 of the movement station 100 works cooperatively with the user interface 104. For example, if a user is detected by the communication interface 106 to be within a determined proximity of the movement station 100 (e.g., beacon technology that "pings" employees when they walk by), the user interface 104 may be activated to remind or otherwise encourage the user to breathe, roll, move, or perform certain health therapy actions.

In some cases, the user interface 104 may be arranged to present multimedia content to a user (e.g., one or more of videos, audio, or other multimedia). The multimedia content may include health related information, video games that encourage or require performance of health therapy actions or other health-related activities, or other such content. In these or other cases, the user interface 104 may be used to accept user input representing identification, personal preferences, health questions, health conditions, or other user information.

Figure 2:
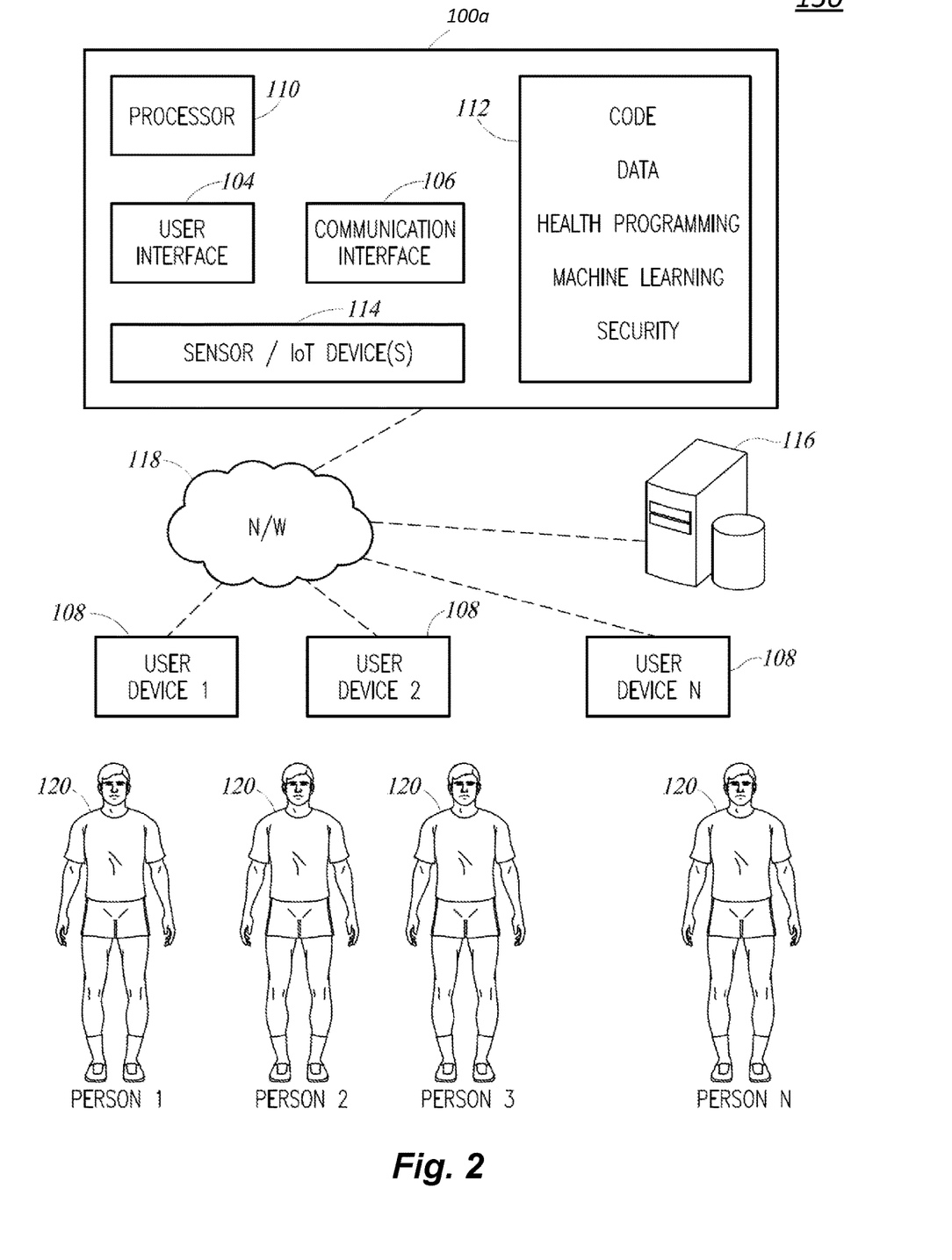
FIG. 2 is an interactive health therapy system.

FIG. 2 is an interactive health therapy system. The system includes a movement station 100 and one or more mobile computing devices 108. To simplify the discussion herein, each of a plurality of mobile computing devices (i.e., User Device 1, User Device 2, . . . User Device N) is identified as mobile computing device 108. It is recognized that each of the computing devices may be differently arranged in size, computing resources, configuration, and the like. For example, some of the mobile computing devices may be smart phones, others may be wearable computing appliances (e.g., smart watch, smart bracelet, smart clothing, and body-worn computing devices), still others may be tablet computers, and other types of devices are contemplated as well.

The movement station 100 of FIG. 2 is the movement station of FIG. 1 shown with a different level of detail. The movement station 100 includes the user interface 104, communication interface 106, a processor 110, a memory 112, and one or more sensor devices 114, which may be arranged individually or collectively as Internet of Things (IoT) devices.

The memory 112 of movement station 100 may include executable software instructions (i.e., "code"), which, when executed by the local processor 110 alone or in cooperation with other code that is remotely executed (e.g., cloud computing, distributed computing, server-farm computing, multi-processor computing, or the like), carry out one or more acts of a method of interactive health therapy. The memory 112 may also include data associated with the one or more acts of a method of interactive health therapy. Particular health programming, machine learning, and security logic may also be stored or otherwise associated with memory 112. In some cases, the health programming logic, machine learning logic, and the security logic may include or be formed with one or more separate hardware circuits. In these or other implementations, the health programming logic, machine learning logic, and security logic, individually or collectively, may comply with regulations of a government body (e.g., privacy, Health Insurance Portability and Accountability Act (HIPAA), or the like).

The movement station 100 may be programmed to communicate via communication interface 106, through a network 118, to a computing server 116 and any determined number of mobile computing devices 108. One of skill in the art will recognize that the computing server 116 and the mobile computing devices 108 include at least one processor, memory, communications interface, and other such essential computing circuitry, but that such circuitry is not shown in FIG. 2 to avoid complicating the drawings and obscuring certain features. In at least some cases, the computing server 116 is arranged as a cloud computing platform, distributed computing platform, server-farm computing platform, multi-processor computing platform, or the like. In at least some of these or other cases, the computing server 116 hosts a user profile database that stores input data, output data, and generated data of a plurality of personalized movement health programs associated respectively with a plurality of users.

Each computing device 108 is arranged to locally or remotely execute operations of an interactive health therapy client program. The interactive heath therapy client program may be a software program (i.e., an application) loaded on the respective computing device 108. In addition, or in the alternative, the interactive heath therapy client program may be executed on a remote computing device (e.g., computing server 116) and accessed via a transceiver of the respective computing device 108.

The movement station 100 is arranged to provide individual users (e.g., employees) with personalized education and resources needed to reduce their risk of musculoskeletal disorders (MSDs) such as those described in the present disclose (e.g., low back pain, neck tension, carpal tunnel syndrome, and many others). The movement station 100 brings "movement health" to users in a workplace and gives consumers and businesses access to tools to improve their movement health and reduce the occurrence of MSDs.

As now known, one in two Americans report musculoskeletal pain with an annual cost to the United States economy of $796 billion (5.7% GDP). MSDs remain challenging to prevent and treat as MSDs often stem from multiple underlying causes. Compounding these factors is the heretofore absence of personalized solutions and resources related to injury prevention. This absence of personalized solutions, which also includes an absence of preventative tools, has resulted in a reactive model of medical treatment, which drives an increase in medical costs related to MSDs.

Using the teaching of the present disclosure, users can be provided with information identifying early warning signs of MSD and information representing personalized prevention strategies to alleviate, slow, or even reverse the MSD, which is rooted in cutting-edge physiology research for both the work and home environments. Hence, the movement stations 100 described in the present disclosure provide at least one solution to helping users address early warning signs of potential injuries. Giving users access to the movement station 100, particularly at work and in some cases at home, gives them the tools they need to address their movement health.

In some embodiments, a movement station 100 is optionally arranged for "workplace" use, and in some embodiments, a movement station 100 is optionally arranged for "home" use. In this way, a user is empowered to take steps to maintain her musculoskeletal health while she is at her desk and while she is otherwise relaxing at home.

According to the Occupational Safety and Health Administration, (OSHA) and the Bureau of Labor and Statistics, currently over 33% of all worker compensation claims are related to MSD, with the average cost of one MSD equal to $70,000. Use of one or more workplace embodiments of the movement stations 100 and associated operations described herein may reduce incident rates, reduce insurance premiums, and increase quality of life for employees and revenue for the employer.

Individuals have not heretofore had access to a personalized movement health program and related movement tools through a personalized prevention plan on an associated computing device 108 (e.g., smartphone). The systems, devices, and methods described herein may provide users with information and education needed to integrate MSD prevention into their daily life.

In some cases, the interactive heath therapy client program, resident or otherwise associated with a computing device 108, permits a user to set personal preferences as to the areas of their body that are suffering or otherwise exhibiting systems of one or more MSDs. The interactive heath therapy client program is arranged to communicate ideas, steps, or specific activities for the user to take in order to reduce the MSDs in one or more body areas. For example, if a first user feels a sore neck while working at her computer all day long, the first user would like to know how to prevent soreness and stiffness in her neck. In this case, the first user can enter her preference in the interactive heath therapy client program of the computing device 108 that she wants more information on "neck soreness" and receive data representing preventative exercises that she can do on a daily basis.

To implement these features, the interactive heath therapy client program of the computing device 108 communicates with a corresponding program of the movement station 100 via communication interface 106. When a user is within a determined proximity of the movement station 100, which may be a user adjustable proximity, the movement station 100 will retrieve the user's preferences. One or both of the user interface 104 and the computing device 108 may be arranged to display or otherwise communicate how to use a particular piece of health therapy equipment. For example, if a second user gets up from his desk (e.g., to use the restroom or for some other reason), and if the second user gets "close" to the movement station (e.g., close enough to trigger a sensor/IoT device 114 or within a user-defined proximity such as five feet, ten feet, in the same room, or some other proximity), the movement station 100 will identify the second user and retrieve his preferences or other information associated with him. Through the logic of memory 112, the movement station 100 will detect or otherwise retrieve the data associated with the second user's personal preferences. If, for example, the second user wants to know how to prevent stiffness/soreness in his arms and hands, the movement station 100 may also know this information and display instructions for use of a particular tool, specifically for hand and wrist or arm stiffness/soreness. In some cases, these functions are provided by a set of rules embodied in the code of memory 12 or in the health programming logic of memory 112. In other cases, the machine learning logic of memory 112 may over time "learn" particular preferences and needs of the second user and thereby automatically provide information when the second user is detected. In some cases, the learning may include the second user providing input information to the movement station 100 (e.g., whether a particular piece of health therapy equipment was effective, how much the second user liked or disliked the equipment, how much the second user used the equipment, and the like). In these or other cases, the learning may include the movement station 100 retrieving information generated by one or more sensors integrated or otherwise associated with the particular piece of health therapy equipment. The sensors in these cases may optionally generate data counting repetitions, determining orientation of the equipment during use, determining one or more forces that the second user subjected the equipment to, and the like.

Figure 3:
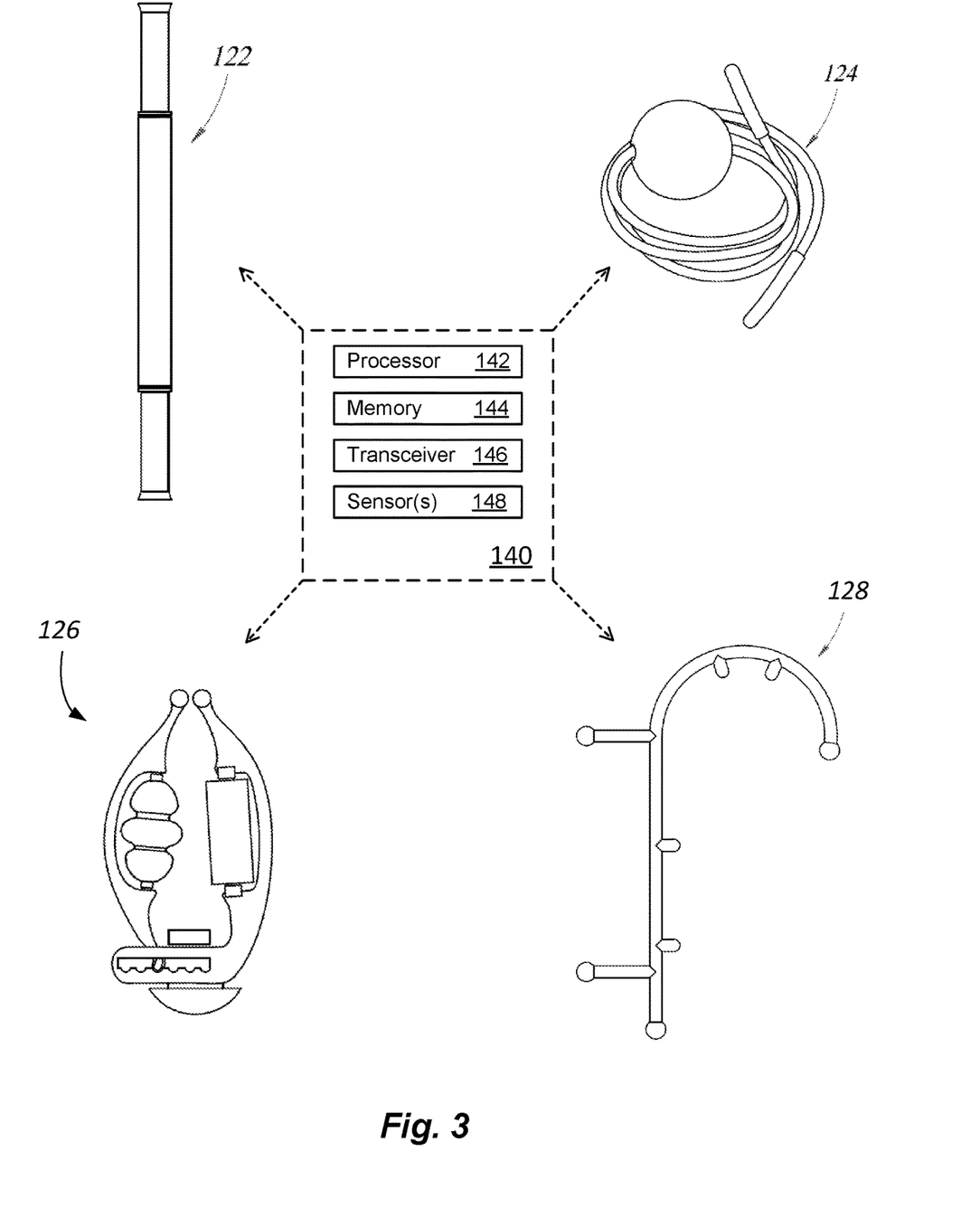
FIG. 3 is a non-limiting selection of health therapy equipment.

FIG. 3 is a non-limiting selection of health therapy equipment. Some or all of the individual pieces of health therapy equipment of FIG. 3 may be stored in receptacles such as the recessed compartments 102 or attachment points 132 of a movement station 100. In some cases, two or more of the same pieces of health therapy equipment may be provided. When a plurality of the same pieces are provided, one or more of the plurality may be identical, or one or more may have different dimensions, colors, textures, materials, or other characteristics. A first piece of health therapy equipment in FIG. 3 is a massage roller 122 (18×1.5×1 inches), a second piece of health therapy equipment is a massage ball 124 (3×3×3 inches), a third piece of health therapy equipment is an arm roller 126 (16×8.25×3.75 inches), and a fourth piece of health therapy equipment is a massage cane 128 (24×15×1 inches). Other types and forms of health therapy equipment are of course contemplated. In fact, health therapy equipment of nearly any type may be accessible via a movement station 100 as described herein.

In some cases, a piece of health therapy equipment includes electronic circuitry 140 arranged to cooperate with the movement station 100, a mobile computing device 108, or other computing devices. In some cases, the health therapy equipment may be an Internet of Things (IoT) device. In this way, the health therapy equipment is individually and in some cases uniquely identifiable on a communications network. These features of the health therapy equipment may permit health therapy that is customized to a particular user. For example, the movement station 100, a mobile computing device 108, or some other computing device may provide instruction for using the health therapy equipment or motivational messaging content (e.g., voice, video, tactile signals) to encourage use of the health therapy equipment. The circuitry may also be used for other purposes such as to facilitate a local or remote record of use of the health therapy equipment, anti-theft features, structural integrity features, useful life monitoring of the health therapy equipment, and other such uses.

Optionally, any of the health therapy equipment pieces illustrated and otherwise described in the present disclosure may include certain electronic circuitry 140. The dashed lines of the electronic circuitry 140 of FIG. 3 indicate the optionality of any particular circuits in the health therapy equipment.

The electronic circuitry 140 of FIG. 3 includes a processor 142, memory 144, a transceiver 146, and any number and type of sensors 148. The memory may store a type identifier (e.g., a number, an alphanumeric value, a text string, or the like) for the type of equipment (e.g., massage roller, massage ball, arm roller, massage cane, step box, acupressure device, squeeze device, electronic pulse massager, heating pad, bolster, and any other type of health therapy equipment). The memory may also or alternatively store a system-wide unique device identifier to distinguish each piece of health therapy equipment. In addition, the memory may store processor-executable instructions that direct the electronic circuitry 140 to communicate, via a transceiver to an external computing device such as the movement station 100, a mobile device 108, or some other computing device.

The sensors 148 of the electronic circuitry 140 may be any type of sensors. For example, the sensors 148 may comprise one or more microelectromechanical system (MEMs) devices, and such devices may be arranged to capture or otherwise generate data associated with an orientation of the device, motion of the device, direction of the device, stress (e.g., bending, twisting, rolling, compressing, and the like) on the device, number of repetitions performed with the device, and the like. Other sensors may capture or otherwise generate temperature, humidity, other environmental data, time data, date data, and the like.

Considering one exemplary but not limiting and not exhaustive cases, a particular health therapy device such as a massage roller 122 includes the electronic circuitry 140 of FIG. 3. When the massage roller 122 is stored or otherwise present in the movement station 100, the device will communicate with movement station 100. The communication may include the transfer of a type identifier (e.g., "18 inch massage roller"), a specific device identifier (e.g., MR1, MR4, or the like), and sensor data. When a user interacts with the movement station 100, the user may remove the massage roller at his own discretion or with encouragement from the movement station 100, and in this case, the movement station 100 may couple information identifying the user with the specific health therapy device (i.e., the massage roller 122 in this example). The user uses the health therapy device in proximity to the movement station 100 or in some other location, and during use, the electronic circuitry 140 of the device captures or otherwise generates usage data. For example, the sensors 148 may capture motion of the device, number of rolls of the device, direction of rolls of the device, compression or some other pressure measurement indicating how passively or aggressively the user is using the massage roller 122, duration of use, number of starts and stops of the device, and the like. Subsequently, when the user returns the massage roller 122 to the movement station 100, the movement station 100 will communicate with the massage roller 122 and receive the sensor information from the device. The sensor information may be used by the movement station 100 to improve or otherwise adapt and evolve a personalized movement health program for the specific user.

Figure 4:
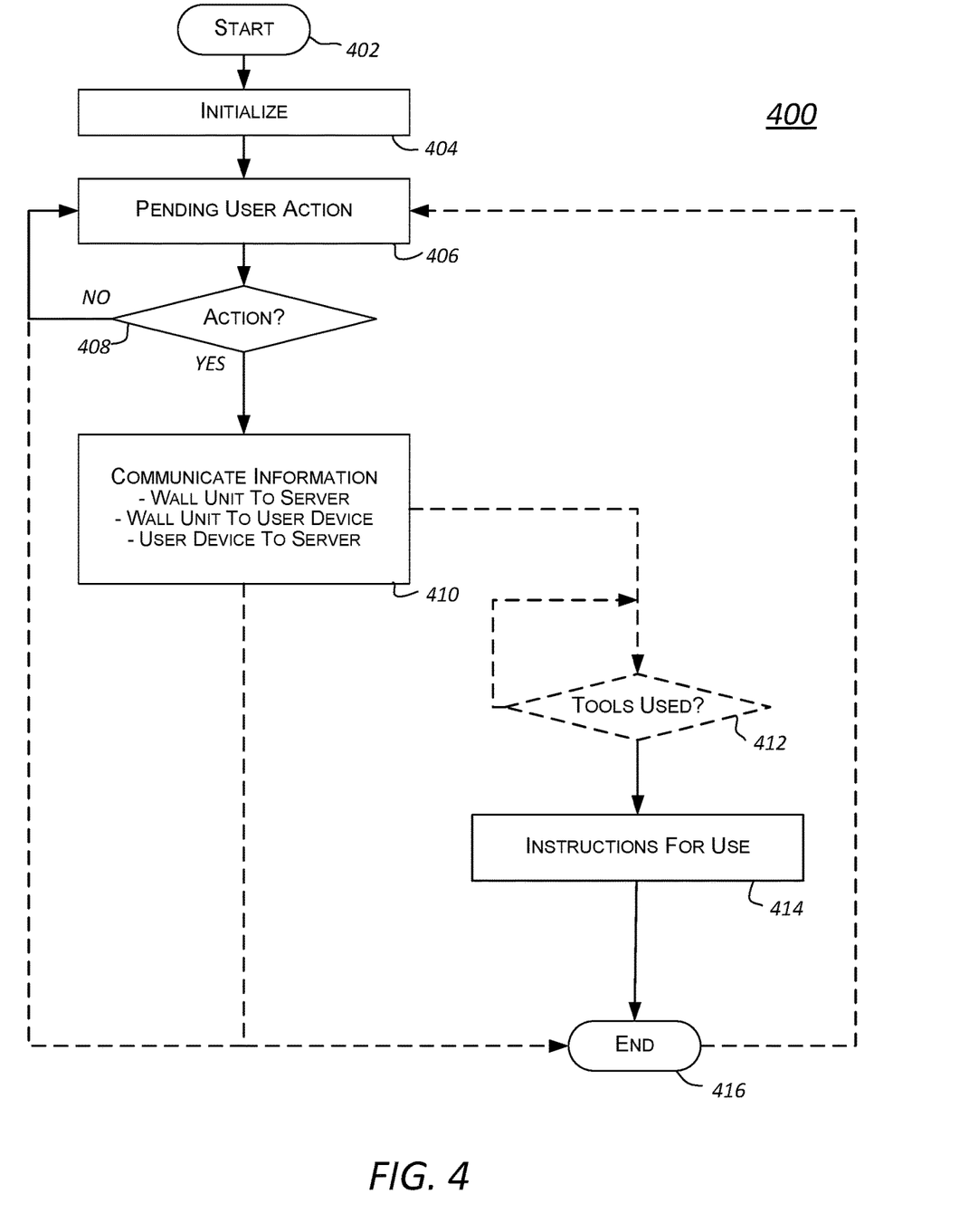
FIG. 4 is a data flow embodiment showing use of a movement station for interactive health therapy.

FIG. 4 is a data flow embodiment 400 showing use of a movement station 100 for interactive health therapy. The embodiment makes reference to the structures of FIGS. 1-3. In the embodiment, particular devices are called out to assist in understanding the inventive concepts of the present disclosure, however, it is understood that the devices as used in the discussion of FIG. 4 are not so limited. For example, in the discussion of FIG. 4, a mobile computing device 108 is described as a smartphone. It is understood that a mobile computing device 108 may be a smartphone, a tablet computing device, a wearable computing device, smart clothing, smart jewelry, or any device with computing capabilities that may interact with a movement station 100, health therapy equipment, a remote computing server 116, and the like.

Processing in the data flow embodiment 400 begins at 402.

At 404, one or more of the interactive health therapy systems are initialized. The initialization acts may include initialization of the movement station 100 computing resources, computing device 108 computing resources, and the resources of the computing server 116.

When the movement station 100 initializes, a user interface may communicate multimedia content such as a display of capabilities of the movement station, motivational encouragement for healthy movement, instructions to breathe, roll, move, or perform certain health therapy actions, or some other content. The user interface 104 may communicate, for example, advertising, corporate branding, news, or other any other information. In some cases, the user interface permits one or more users of the movement station 100 to enter specific user information such as identification, status, results of past health therapy, scheduling for future health therapy, questions, concerns, and the like. Other initialization of the movement station 100 may include resetting certain data, updating of one or more health programs, downloading or processing of training information for the machine learning logic, security verification of private user information, and security verification of the health therapy equipment 122-128 stored in the receptacles (e.g., recessed compartments 102, attachment points 132, and the like). In some cases, the communication interface 106 of the movement station 100 communicates with remote computing server 116 to retrieve updated health programming information, new user data, system-wide directives, remote management directives, and the like. Initialization of the movement station may also include initialization of one or more sensor circuits 114. The sensors may provide information to the processor 110 indicating if any users are detected in proximity to the movement station 100.

Initialization of the mobile computing devices 108 may include starting or otherwise accessing an application that will communicatively interact with the movement station 100. The mobile computing device 108 may also communicate stored data to the remote computing server 116 and receive new information from the remote computing server 116.

Processing falls to 406 where the interactive health therapy system waits, pending for user action. While the system is pending, the movement station 100 may continue to provide information via the user interface 104, or the movement station 100 may enter a sleep mode. In some cases, the pending state at 406 is further controlled by a timer (e.g., sleep during non-business hours), ambient light sensor circuitry (e.g., sleep when the immediate area surrounding the movement station is dark), or in other cases. Also while the system is pending, the remote computing devices 108 may be outside of a detectable range of the movement station, disabled by a user interaction, or pending for other reasons.

At 408, one or more events occur to cause action of the interactive health therapy system. For example, the event may be a user entering a health related question or comment into their smartphone (i.e., mobile computing device 108). Another exemplary event is the user walking near the movement station 100. In this case, the sensor device 114 of the movement station 100 detects the smartphone of the user, and the user is uniquely identified by the movement station 100.

Based on the detection of action at 408, processing falls to 410 where any two or more of the movement station 100, remote computing server 116, and smartphone communicate information between each other. The communicated information may include user identification, user preferences, user questions, user concerns, scheduled health therapy, collected results of previous health therapy, or any other information.

From 410, processing will optionally advance back to 406, where the system is pending, to 412, where a user will interact with one or more pieces of health therapy equipment, or to the end of processing at 416.

If the movement station 100 has detected the smartphone of a particular user, processing at 412 may begin. Here, the user may be encouraged, instructed, or otherwise inspired to interact with at least one piece of health therapy equipment. The user may select a piece of equipment from a recessed compartment 102 or attachment points 132 as directed by a health program. In some cases, the movement station 100 will communicate directly with the selected piece of health therapy equipment via the electronic circuitry 140 of the selected equipment.

Processing at 414 may be directed by the health programming logic of movement station 100. The health programming logic may provide instructions for use of the health therapy equipment, automatic counting, recordation of repetitions, or recording of other status capturing events.

At 416, processing may end. Optionally, processing may also return to 406 pending additional user action.

Figure 5:
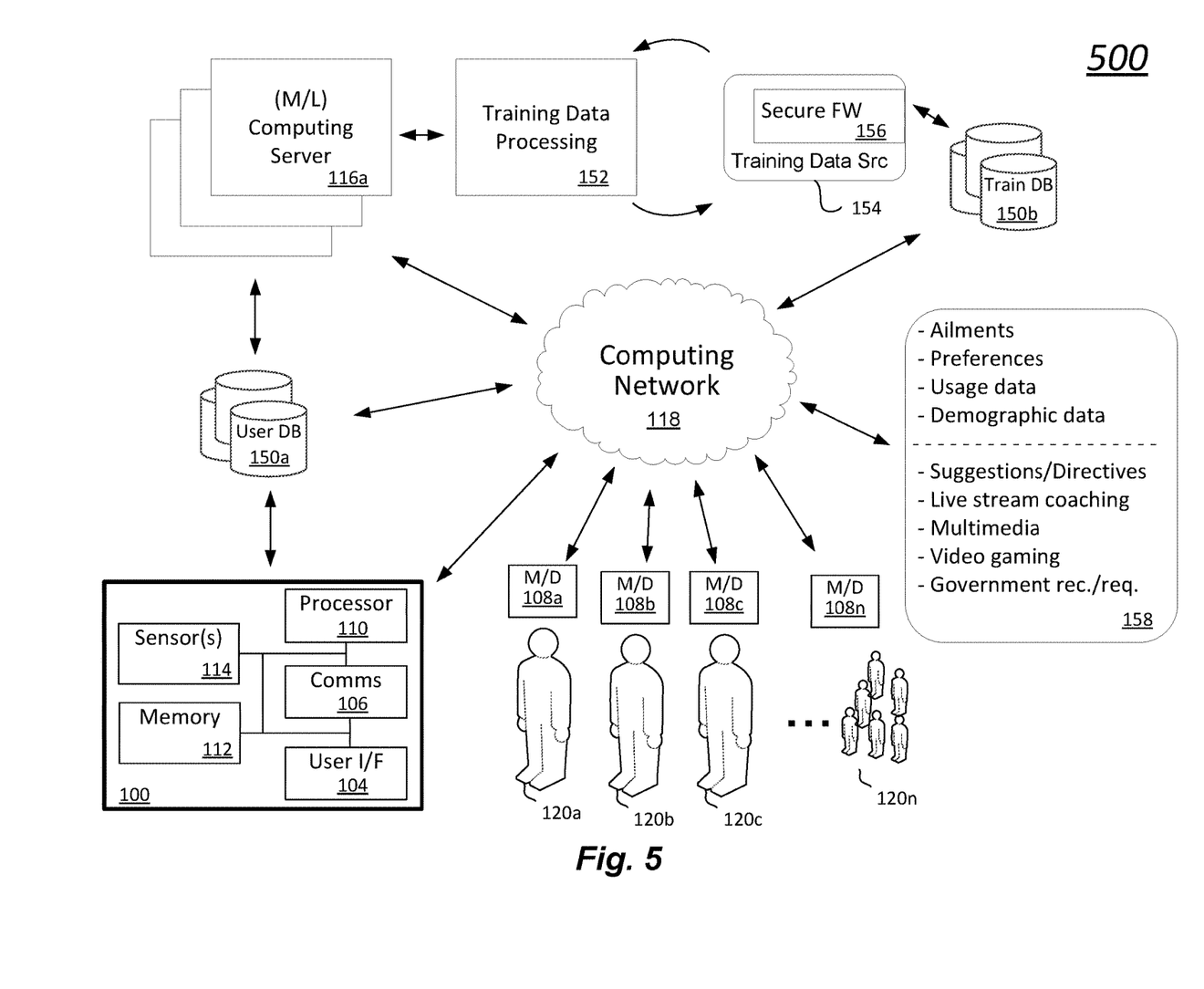
FIG. 5 is another data flow embodiment showing use of a movement station for interactive health therapy.

FIG. 5 is another data flow embodiment 500 showing use of a movement station 100 for interactive health therapy. Along the lines of FIG. 4, the data flow embodiment 500 of FIG. 5 makes reference to the structures described in the present disclosure; however, at least some description is not repeated for brevity.

The movement station 100 of FIG. 5 is arranged to contain a plurality of health therapy devices in any suitable number and form of receptacles. The movement station 100 may include or otherwise be arranged as a self-contained computing device. Alternatively, the movement station may include some computing functions that interact with a remote computing server device 116a, which is along the lines of the computing server 116 (FIG. 2). The computing server 116a, and additionally or alternatively the computing structures of the movement station 100 may be arranged according to direct programming computing principles. In this respect, the direct programming principles accept input data, apply rules that implement one or more interactive health therapy programs, personalized movement health programs, or the like.

In other embodiments, the computing server 116a is arranged as a machine learning (e.g., artificial intelligence) device that cooperates with the computing structures of the movement station 100 to implement one or more interactive health therapy programs, personalized movement health programs, or the like. In these machine learning embodiments, the computing server 116a is arranged to accept user data, training data, and any other suitable data and dynamically adapt its programming models to predict user health ailments, suggest certain health therapy equipment, provide timing, routines, and other such instructional information to encourage users to remove a selected health therapy device from the movement station 100 and use the selected device.

Using either the rules-based programming models or the machine learning models described herein, the teaching of the present disclosure enables movement station embodiments that contain a collection of injury prevention tools (i.e., health therapy devices) to interact with mobile devices 108 of any number of a plurality of users 120a, 120b, 120c, 120n. The embodiments accept user input describing one or more body parts that the user would like to address (e.g., reduce stiffness and soreness), accept user input that describes the user's daily activity (e.g., sitting, driving, standing, walking, bending, and the like), and accept other such user data. In at least some cases, the systems are also arranged to accept subjective user data such as the user's personal preferences, health goals, and health limitations. Using this information, the movement stations may unidirectionally or bi-directionally remind individuals at the determined times, which may be user selectable, to perform stiffness/soreness prevention activities using one or more health therapy devices contained at the movement station, communicate recommendations or other helpful advice to perform particular activities with the one or more health therapy devices, (e.g., drink water, rest, accelerate, slow down, and the like), and provide personalized coaching to each particular user. The information may be accepted and delivered via voice input/output, touch screen, or other human interface devices. In at least some cases, personalized coaching, which may be live, recorded, or even computer generated, may be delivered via a user interface 104 of the movement station or a user interface to the user's mobile device.

In addition to the plurality of users 120a-120n and their respective mobile devices 108a-108n, and in addition to the movement station 100, the data flow embodiment 500 of FIG. 5 includes at least two computer-accessible repositories; a first user profile database 150a and a second training data database 150b. The embodiment includes a computing server 116a that may be arranged as a machine learning device 116a, and in these cases, the computing server may cooperate with logic that includes a training data processing module 152 and a training data source module 154. The training data source module 154 receives a flow of training data, which may include real user data, from a training data database 150b. For these reasons, an optional secure framework module 156 may be used to obfuscate, anonymize, or otherwise operate to keep the system in compliance with standard security practices, industry-acceptable privacy practices, government requirements (e.g., Health Insurance Portability and Accountability Act (HIPAA)), and the like.

In particular usage, the training data in the training data database 150b may include demographic data, health data, known injury data, objective sedentary lifestyle data, range of activity data, and the like. Hundreds, thousands, millions, tens of millions, and even greater numbers of datapoints may be stored in the training data database 150b and communicated in a determined way to the training data source module 154. The training data secure framework module 156 may encrypt data, decrypt data, strip personally identifiable information, or perform other security tasks. In single or multiple processing passes (e.g., repeatedly, iteratively, continuously, or the like), the training data processing module 152 and training data source module 154 perform analysis on the input data. The analysis may in some cases perform convolutional neural network processing along the lines of machine vision algorithms which permit any suitable set of input factors to be dynamically analyzed to generate suggested movement health model activity for any particular user.

In the unidirectional or bidirectional messaging 158, a user may, via their mobile computing device 108 or via the movement station, provide input information regarding ailments, preferences, health therapy device usage data, demographic data, and other suitable data. The movement station 100, via cooperation individual processing or via cooperation with the computing server 116a, provide suggestions or directives to the user for use of particular health therapy devices, live stream coaching, multimedia instructions or other guidance, health-related and healthy activity base video gaming, government recommendations, government requirements, and the like.

Particular non-limiting usage embodiments and data processing is now provided to further illuminate the novel and non-obvious subject matter of the present disclosure.

The embodiment 500 of FIG. 5 may be described as an interactive health therapy system. The movement station 100 may be positioned in an office setting, warehouse setting, or other workplace environment which is frequented by employees of the business. In some but not all cases, various features of the movement station are arranged for improved accessibility to a user standing or walking in proximity to the movement station 100. The movement station may be a freestanding unit that is several feet (e.g., three feet, five feet, seven feet, or some other linear distance) in height, and several feet (e.g., smaller, larger, or the same distance as the height) in width. The depth of the movement station 100, like the height and width, may be any suitable distance such as two feet, four feet, or some other distance in depth. Alternative to a freestanding unit, the movement station may be against a wall, mechanically, or in some cases electromechanically, mounted to a wall, integrated into a wall, or integrated into some other structure. The movement station may be aesthetically shaped, colored, decorated, or arranged with other visually desirable characteristics. In at least some cases, the movement station will have a color scheme or other like decorative features that may be aligned with a sports team popular in the local area of installation. In this way, the decorative features may play a utilitarian role of calling to a plurality of employees' mind ideas of fitness, strength, speed, and other desirable health attributes.

The movement station 100 may further be arranged with any suitable number of health therapy device storage areas (i.e., receptacles) arranged to store or otherwise contain a plurality of health therapy devices. Computationally, the movement station 100 is arranged with a memory 112, a processor 110 coupled to the memory 112 and arranged to administer a plurality of personalized movement health programs via processor-executable instructions stored in the memory 112, a user interface 104 communicatively coupled to the processor 110 and arranged to interact with a plurality of employee users that may each have their own personalized movement health program, any suitable number of sensors 114, and a communication interface 106.

In operation, any number of employees may be inducted into the movement station system. The induction process may include capturing, collecting, or otherwise receiving personal data regarding the employee. The personal data may include objective human health data such as height, weight, age, average number of steps taken per day, known injuries or MSK health issues, typical hours of work, type of work tasks performed, and the like. The personal data may also or alternatively include subjective human health data such as personal health preferences, hobbies, favorite sports, favorite sports teams, favorite parts of the employee's workday, least favorite sports, least favorite sports teams, least favorite parts of the employee's workday, known changes to health based on activity or absence of activity, and the like. In some cases, the employee's objective and subjective health information may be collected via surveys, pre-prepared fillable forms, a software (e.g., mobile software, web software, or the like) application, or in some other way. In some cases, the collection of the objective and subjective health information is an ongoing process, and the information may be suitably weighted, time-stamped, or curated in other ways.

The objective and subjective employee health information that is collected, like other data of the embodiment 500 of FIG. 5, may be communicated via the network 118 to a remote computing device, processed, and stored in the training data database 150b. This data, individually and collectively, may be used to further train the machine learning logic of the memory 112, the computing server 116a, or another suitable computing system.

When a user (e.g., an employee, a worker, or some other human) comes in proximity of the movement station 100, the remote device 108 or some other sensor-detectable component (e.g., a machine-vision recognizable face, a bio-sensor recognizable body part, a wearable computing device, an ID badge, or the like) is detected by a sensor 114 of the movement station 100. The detection of the particular user may cause the movement station 100 to communicate with the user via information passed through the communication interface 106 to a mobile computing device 108 associated with the user. The movement station 100 may alternatively or additionally communicate with the user via the user interface 104 of the movement station 100.

Based on the identity of the user, based on an interactive health therapy client program running on a mobile device or on a remote device, based on a personalized movement health program, based on a prediction from a machine learning algorithm executing on the remote computing server 116a, or based on something else, the information communicated to the user may be information that encourages the user to remove one or more selected health therapy devices or a certain type of health therapy device from the movement station 100. The health therapy device may be a massage roller, a massage ball, an arm roller, a massage cane, a step box, an acupressure device, a squeeze device, an electronic pulse massager, a heating pad, a bolster, or some other health therapy device (e.g., exemplary and non-limiting health therapy devices of FIG. 3). The single or plurality of health therapy devices may be stored in any suitable type of receptacle of the movement station such a recessed compartment, one or more attachment points (e.g., hooks, pegs, magnets, clips, hook-and-loop areas, or the like). Any or all of the health therapy devices may have integrated sensors that communicatively cooperate with one or more sensors of the movement station 100. The cooperation may be sufficient for the movement station 100 to determine whether a particular health therapy device is "in," "on," or otherwise contained by the movement station 100 or not, such as when the devices are removed by employees for use. Alternatively, or in addition, the cooperation may permit data collected by the sensors of each health therapy device to be communicated to the movement station 100 and used to validate, modify, or otherwise be included in the processing of a user's personalized movement health program.

The sensors 114 of the movement station 100 may be of any suitable type and electronic capability. The sensors 114 may include cameras and associated device recognition or human recognition software, radio frequency identifier (RFID) devices, light-detection devices, WiFi transceivers, BLUETOOTH transceivers, or any other such devices. In some cases, various sensors 114 of the movement station 100 and cooperating software are arranged to detect the removal and subsequent return of selected health therapy devices from the movement station 100. Such sensors may, for example, be integrated or otherwise located in or around the receptacles of the movement station 100. Other sensors 114 of the movement station 100 may include proximity sensors (e.g., RF-based, sound-based, light-based, or the like) that determine when an employee is nearby (e.g., within three feet of the movement station, within ten feet of the movement station, in the same room as the movement station, or the like), proximity sensors that distinguish human-beings from non-human-beings, proximity sensors that determine how many people are in proximity to the movement station, and other such proximity sensors. In some cases, such as when a proximity sensor is implemented via a remotely executed machine vision algorithm, the proximity sensor may be integrated with, or otherwise associated with, the communication interface 106.

Still other sensors 114 and associated programming may be used to direct the movement station to enter, exit, or otherwise operate at different levels of power consumption and different levels of interactively. For example some sensors 114 may include clock functionality that put the movement station 100 into a sleep mode during non-business hours. Some sensors 114 include motion detection to put the movement station 100 into the sleep mode when no users are present and wake the movement station 100 when one or more users are detected. Some sensors 114 include light detection to put the movement station 100 into the sleep mode when ambient light is dimmed or extinguished and wake the movement station 100 when a certain ambient light level is detected. Any one or more of these sensors 114, and other sensors 114 described herein, may permit user or machine configurable thresholds, time windows, intensities, and other such parameters.

Turning back to the example at hand, upon detection of the user in proximity to the movement station 100, and upon encouraging the user to select a particular health therapy device (e.g., according to the user's personalized movement health program), the user will remove the particular health therapy device from the movement station 100, use the particular health therapy device, and return the particular health therapy device to the movement station 100. The personalized movement health program, which may be stored or otherwise administered at the movement station 100, at the remote computing server 116a, or distributed amongst both the movement station 100 and the remote computing server 116, will collect data associated with the user's use of the particular health therapy device. The collected data will be used to update the user's personalized movement health program. In some cases, the particular health therapy device has at least one integrated sensor arranged to generate the data when the particular health therapy device is in use. The data may include or otherwise be associated with a number of repetitions of use of the particular health therapy device, orientation of the particular health therapy device during use, force applied to at least a portion of the particular health therapy device during use, and other such sensor-collected data.

The computing server 116a, when configured as a machine learning computing server, will cooperate with the training data processing module 152. The training data processing module 152 works interactively with the training data source module 154 to process a large (e.g., hundreds, thousands, millions, billions, trillions, or some other number) pool of data records having objective and subjective health information stored therein. Using the objective and subjective health information, the computing server 116a is arranged to administer any number of personalized movement health programs for any number of employees. In this way, based on the processing of training data, the particular user may be encouraged to perform certain health activities such as particular breathing, rolling, stretching, moving, and the like using particular health therapy devices. The direction or other encouragement thus be a result of improved health experiences of other similarly situated and similarly constituted users. The personalized movement health program, or some other interactive health therapy client program, may be arranged to deliver information identifying early warning signs of musculoskeletal disorder (MSD), information representing personalized prevention strategies, or other such information.

In some cases, particular operations of a personalized movement health program are created by the computing server 116a. The computing server 116a, which is configured as a machine learning device in this case, will process objective training data (e.g., height, weight, age, average number of steps per day, and the like), process subjective training data (e.g., hobbies, favorite sports or other activities, and the like), and accept the user's personal preferences, accept information identifying a user's area of MSD. Using such data, the personalized movement health program may identify activities user wants, identify activities user needs, and predict activities that a user will commit to performing and will in fact continue to perform. The personalized movement health program may operate as by rules that adapt and change (i.e., learn) based on the user's preferences and determined likelihood of success. The personalized movement health program may formulate or otherwise operate according to rules that adapt and change based on data captured by sensors associated with the health therapy equipment.

In some cases, the interaction of a particular user with a movement station 100 may be through the user interface 104 of the movement station 100. The user interface 104 may be a communicatively coupled set of particular circuits (e.g., screen, speakers, mouse, keyboard, and the like) in some cases, and in other cases, the user interface 104 may be arranged as a commodity computing device such as a tablet computer. The interaction may include video, audio, and other multimedia that suggests performance of one or more health activities. The interaction in some cases is delivered as an interactive video game that requires performance of at least one health-related activity. In some cases, video games that require health-related activities may be delivered via the movement station 100, via a mobile computing device 108, or delivered in some other way. In at least some cases, multiple employee users may compete or otherwise participate in a same video games that requires health-related activities.

Having now set forth certain embodiments, further clarification of certain terms used herein may be helpful to providing a more complete understanding of that which is considered inventive in the present disclosure.

A non-comprehensive, non-limiting list of computing devices is provided to aid in understanding the bounds of the terms, "computing device" and "mobile computing device," as used herein. Computing devices (i.e., mobile devices) include cell phones, smart phones, flip phone, tablets, phablets, handheld computers, laptop computers, body-worn computers, and the like. Certain other electronic equipment in any form factor may also be referred to as a mobile computing device when this equipment is provisioned for use to execute the health related acts described in the present disclosure. Examples of this other electronic equipment include in-vehicle devices, medical devices, industrial equipment, retail sales equipment, wholesale sales equipment, utility monitoring equipment, and other such equipment used by private, public, government, and other entities.

Computing devices further have a collection of input/output ports for passing data over short distances to and from other computing devices. For example, serial ports, USB ports, WiFi ports, Bluetooth ports, IEEE 1394 FireWire, and the like can communicatively couple the mobile device to other computing apparatuses.

Computing devices may a battery or another power source, and they may or may not have a display. In many mobile devices, a signal strength indicator is prominently positioned on the display to provide network communication connectivity information to the mobile device user.

A cellular transceiver may be included in a computing device to couple the computing device to other communication devices through a cellular-based communication network. In some cases, software and data in a file system are communicated between the mobile computing device and a computing server via a cellular transceiver. That is, bidirectional communication between a mobile devices, other computing devices, and a computing server is facilitated by the cellular transceiver. For example, a computing server may download a new or updated version of software to the computing device over the cellular-based communication network. As another example, the computing device may communicate any other data to the computing server over the cellular-based communication network or another network.

Each computing device client has electronic memory accessible by at least one processing unit within the device. The memory is programmed with software that directs the one or more processing units. Some of the software modules in the memory control the operation of the computing device with respect to generation, collection, and distribution or other use of data. In some cases, software directs the collection of individual datums, and in other cases, software directs the collection of sets of data.

Software may include a fully executable software program, a simple configuration data file, a link to additional directions, or any combination of known software types. When the computing server updates software, the update may be small or large. For example, in some cases, a computing server downloads a small configuration data file to as part of software, and in other cases, computing server completely replaces all of the present software on a computing device with a fresh version. In some cases, software, data, or software and data is encrypted, encoded, and/or otherwise compressed for reasons that include security, privacy, data transfer speed, data cost, or the like.

Processing devices, or "processors," as described herein, include central processing units (CPU's), microprocessors, microcontrollers (MCU), digital signal processors (DSP), application specific integrated circuits (ASIC), state machines, and the like. Accordingly, a processor as described herein includes any device, system, or part thereof that controls at least one operation, and such a device may be implemented in hardware, firmware, or software, or some combination of at least two of the same. The functionality associated with any particular processor may be centralized or distributed, whether locally or remotely. A processor may interchangeably refer to any type of electronic control circuitry configured to execute programmed software instructions. The programmed instructions may be high-level software instructions, compiled software instructions, assembly-language software instructions, object code, binary code, micro-code, or the like. The programmed instructions may reside in internal or external memory or may be hard-coded as a state machine or set of control signals. According to methods and devices referenced herein, one or more embodiments describe software executable by the processor, which when executed, carries out one or more of the method acts.

As known by one skilled in the art, a computing device, including a mobile computing device, has one or more memories, and each memory may comprise any combination of volatile and non-volatile computer-readable media for reading and writing. Volatile computer-readable media includes, for example, random access memory (RAM). Non-volatile computer-readable media includes, for example, any one or more of read only memory (ROM), magnetic media such as a hard-disk, an optical disk, a flash memory device, a CD-ROM, and the like. In some cases, a particular memory is separated virtually or physically into separate areas, such as a first memory, a second memory, a third memory, etc. In these cases, it is understood that the different divisions of memory may be in different devices or embodied in a single memory. Some or all of the stored contents of a memory may include software instructions executable by a processing device to carry out one or more particular acts.

In the present disclosure, memory may be used in one configuration or another. The memory may be configured to store data. In the alternative or in addition, the memory may be a non-transitory computer readable medium (CRM) wherein the CRM is configured to store instructions executable by a processor. The instructions may be stored individually or as groups of instructions in files. The files may include functions, services, libraries, and the like. The files may include one or more computer programs or may be part of a larger computer program. Alternatively or in addition, each file may include data or other computational support material useful to carry out the computing functions of the systems, methods, and apparatus described in the present disclosure.

FIGS. 4 and 5 are a data flow embodiment 400 and a data flow embodiment 500, respectively, illustrating processes that may be used by embodiments of computing devices such as mobile computing device 108, movement station 100, and computing server 116. In this regard, each described process may represent a module, segment, or portion of code, which comprises one or more executable instructions for implementing the specified logical function(s). It should also be noted that in some implementations, the functions noted in the process may occur in a different order, may include additional functions, may occur concurrently, and/or may be omitted.

As used in the present disclosure, the term "module" refers to an application specific integrated circuit (ASIC), an electronic circuit, a processor and a memory operative to execute one or more software or firmware programs, combinational logic circuitry, or other suitable components (hardware, software, or hardware and software) that provide the functionality described with respect to the module.

The terms, "real-time" or "real time," as used herein and in the claims that follow, are not intended to imply instantaneous processing, transmission, reception, or otherwise as the case may be. Instead, the terms, "real-time" and "real time" imply that the activity occurs over an acceptably short period of time (e.g., over a period of microseconds or milliseconds), and that the activity may be performed on an ongoing basis (e.g., recording and reporting the collection of health therapy data and the like). An example of an activity that is not real-time is one that occurs over an extended period of time (e.g., hours or days)] or that occurs based on intervention or direction by a person or other activity.

Where the terms "substantial" or "about" in any grammatical form are used as modifiers in the present disclosure and any appended claims (e.g., to modify a structure, a dimension, a measurement, or some other characteristic), it is understood that the characteristic may vary by up to 30 percent. For example, a movement station 100 may be described as being mounted "substantially vertically," In these cases, a device that is mounted exactly vertical is mounted along an "X" axis and a "Y" axis that is normal (i.e., 90 degrees or at right angle) to a plane or line formed by a "Z" axis. Different from the exact precision of the term, "vertical," and the use of "substantially" or "about" to modify the characteristic permits a variance of the particular characteristic by up to 30 percent. As another example, a movement station 100 having a particular linear dimension of twice as tall as is wide includes such devices in which the linear dimension varies by up to 30 percent.

The terms "include" and "comprise" as well as derivatives thereof, in all of their syntactic contexts, are to be construed without limitation in an open, inclusive sense, (e.g., "including, but not limited to"). The term "or," is inclusive, meaning and/or. The phrases "associated with" and "associated therewith," as well as derivatives thereof, can be understood as meaning to include, be included within, interconnect with, contain, be contained within, connect to or with, couple to or with, be communicable with, cooperate with, interleave, juxtapose, be proximate to, be bound to or with, have, have a property of, or the like.

Unless the context requires otherwise, throughout the specification and claims which follow, the word "comprise" and variations thereof, such as, "comprises" and "comprising," are to be construed in an open, inclusive sense, e.g., "including, but not limited to."

Reference throughout this specification to "one embodiment" or "an embodiment" and variations thereof means that a particular feature, structure, or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

As used in this specification and the appended claims, the singular forms "a," "an," and "the" include plural referents unless the content and context clearly dictates otherwise. It should also be noted that the conjunctive terms, "and" and "or" are generally employed in the broadest sense to include "and/or" unless the content and context clearly dictates inclusivity or exclusivity as the case may be. In addition, the composition of "and" and "or" when recited herein as "and/or" is intended to encompass an embodiment that includes all of the associated items or ideas and one or more other alternative embodiments that include fewer than all of the associated items or ideas.

In the present disclosure, conjunctive lists make use of a comma, which may be known as an Oxford comma, a Harvard comma, a serial comma, or another like term. Such lists are intended to connect words, clauses or sentences such that the thing following the comma is also included in the list.

As described herein, for simplicity, a user is in some case described in the context of the male gender. For example, the terms "his," "him," and the like may be used. It is understood that a user can be of any gender, and the terms "he," "his," and the like as used herein are to be interpreted broadly inclusive of all known gender definitions.

As the context may require in this disclosure, except as the context may dictate otherwise, the singular shall mean the plural and vice versa; all pronouns shall mean and include the person, entity, firm or corporation to which they relate; and the masculine shall mean the feminine and vice versa.

When so arranged as described herein, each computing device may be transformed from a generic and unspecific computing device to a combination device comprising hardware and software configured for a specific and particular purpose. When so arranged as described herein, to the extent that any of the inventive concepts described herein are found by a body of competent adjudication to be subsumed in an abstract idea, the ordered combination of elements and limitations are expressly presented to provide a requisite inventive concept by transforming the abstract idea into a tangible and concrete practical application of that abstract idea.

The headings and Abstract of the Disclosure provided herein are for convenience only and do not limit or interpret the scope or meaning of the embodiments.

The various embodiments described above can be combined to provide further embodiments. Aspects of the embodiments can be modified, if necessary to employ concepts of the various patents, application and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. An interactive health therapy system, comprising:
   a plurality of health therapy devices; and
   a movement station having:
      a plurality of health therapy device storage areas arranged to store the plurality of health therapy devices;
      a memory;
      a processor coupled to the memory and arranged to administer a plurality of personalized movement health programs via processor-executable instructions stored in the memory;
      a user interface communicatively coupled to the processor and arranged to interact with a plurality of users associated, respectively, with the plurality of personalized movement health programs;
      a communication interface; and
      at least one sensor, wherein some of the processor-executable instructions, when executed, cause the processor to:
         identify a mobile computing device associated with a first user of the plurality of users;
         select a health therapy device of the plurality of health therapy devices for the first user;

indicate the selected health therapy device to the first user;
communicate with the first user via information passed through the communication interface to the mobile computing device, said information encouraging the first user to remove the selected health therapy device from the movement station;
detect the removal of the selected health therapy device via data from the at least one sensor;
detect the subsequent return of the selected health therapy device via data from the at least one sensor; and
update a first user movement health program of the plurality of personalized movement health programs with data based on detecting the removal and subsequent return of the selected health therapy device, said first user movement health program associated with the first user.

2. The system of claim 1 wherein the plurality of health therapy devices includes one or more of a massage roller, a massage ball, an arm roller, a massage cane, a step box, an acupressure device, a squeeze device, an electronic pulse massager, a heating pad, and a bolster.

3. The system of claim 1 wherein the plurality of health therapy device storage areas includes a plurality of receptacles integrated into the movement station.

4. The system of claim 1 wherein the plurality of health therapy device storage areas includes a plurality of attachment points arranged on an external surface of the movement station.

5. The system of claim 1 wherein the data used to update the first user movement health program is retrieved by the movement station from the selected health therapy device.

6. The system of claim 5 wherein the selected health therapy device has at least one integrated sensor arranged to generate the data when the selected health therapy device is in use.

7. The system of claim 6 wherein the data generated by the at least one integrated sensor of the selected health therapy device is data associated with at least one of repetitions of use of the selected health therapy device, orientation of the selected health therapy device during use, and force applied to at least a portion of the selected health therapy device.

8. The system of claim 1 wherein updating the first user movement health program with the data includes causing the first user movement health program to provide to the first user second information encouraging the first user to remove a different health therapy device of the plurality of health therapy devices from the movement station.

9. The system of claim 1 wherein some of the processor-executable instructions, when executed, further cause the processor to:
accept user input data from the first user, said user input data identifying preferences of the first user; and
generate predicted movement activities of interest for the first user based on the identified preferences of the first user.

10. The system of claim 9 wherein the predicted movement activities of interest for the first user includes at least one video game presented via the user interface of the movement station or the mobile computing device associated with the first user that requires performance of at least one health-related activity.

11. An interactive health therapy method, comprising:
determining that a known user is in proximity to a movement station, the movement station having a plurality of receptacles to store a plurality of health therapy devices;
selecting a health therapy device of the plurality of health therapy devices for the known user;
indicating the health therapy device to the first user via the movement station;
based on an identity of the known user and a personalized movement health program associated with the known user, communicating information to the known user via a communication interface, the information recommending usage of a certain type of the selected health therapy device;
detecting, via first sensor data generated by a first sensor associated with the movement station, removal of a selected health therapy device of the certain type from the movement station;
subsequent to detecting the removal of the selected health therapy device, detecting, via second sensor data generated by a second sensor associated with the movement station, replacement of the selected health therapy device at the movement station; and
updating movement information in the personalized movement health program associated with the known user.

12. The method of claim 11 wherein the first sensor and the second sensor are a same sensor.

13. The interactive health therapy method of claim 11 wherein updating movement information in the personalized movement health program includes:
capturing data generated by at least one sensor associated with the selected health therapy device; and
accepting user input data, said user input data manually provided and associated with usage of the selected health therapy device.

14. The interactive health therapy method of claim 11 wherein updating movement information in the personalized movement health program includes:
capturing data generated by at least one sensor associated with the selected health therapy device.

15. The interactive health therapy method of claim 11, further comprising:
communicating second information to the known user via the communication interface, the second information recommending usage of a second certain type of health therapy device, said second certain type of health therapy device selected based on the updated movement information.

16. A non-transitory computer-readable storage medium whose stored contents configure a computing system to perform a method of interactive workplace health therapy, the method comprising:
providing a movement station, the movement station having a memory arranged to store data and a plurality of processor-executable software instructions, a processor coupled to the memory an arranged to execute at least some of the plurality of processor-executable software instructions, a user interface communicatively coupled to the processor, a communication interface, and at least one sensor arranged to detect a mobile computing device;
providing at least one piece of health therapy equipment in a receptacle of the movement station;
detecting the mobile computing device with the sensor of the movement station when the mobile computing device is in proximity of the movement station;

identifying a user associated with the mobile computing device;

based on the identity of the user, retrieving user profile information from a user profile database;

selecting a health therapy equipment for the user based on the retrieved user profile information;

indicating the selected health therapy equipment to the user via the movement station;

presenting at least one directive to the identified user via the user interface, the directive instructing the user in the use of the at least one piece of health therapy equipment;

collecting information regarding the user's use of the at least one piece of health therapy equipment; and storing the collected information in the user profile database.

17. The non-transitory computer-readable storage medium according to claim 16 whose stored contents configure the computing system to perform the method, wherein the receptacle of the movement station is a recessed receptacle and at least some portion of the recessed receptacle is sized and shaped to match a determined piece of health therapy equipment.

18. The non-transitory computer-readable storage medium according to claim 16 whose stored contents configure the computing system to perform the method, wherein the user profile database is hosted by a remote computing server.

19. The non-transitory computer-readable storage medium according to claim 16 whose stored contents configure the computing system to perform the method, wherein presenting the at least one directive to the identified user includes presenting the at least one directive via the user interface of the movement station.

20. The non-transitory computer-readable storage medium according to claim 16 whose stored contents configure the computing system to perform the method, wherein presenting the at least one directive to the identified user includes presenting the at least one directive via the mobile computing device.

21. The interactive health therapy system of claim 1, wherein causing the processor to update the first user health movement program further comprises causing the processor to:

receive movement data via at least one sensor coupled to the selected health therapy device; and modify at least one health movement activity included in the first user health movement program.

* * * * *

UNITED STATES PATENT AND TRADEMARK OFFICE
CERTIFICATE OF CORRECTION

PATENT NO. : 11,335,449 B2
APPLICATION NO. : 16/428779
DATED : May 17, 2022
INVENTOR(S) : Dana Rindal et al.

Page 1 of 1

It is certified that error appears in the above-identified patent and that said Letters Patent is hereby corrected as shown below:

In the Claims

Column 24, Claim 11, Line 13:
"usage of a certain type of the selected health" should read: -- usage of the selected health --.

Signed and Sealed this
Twenty-third Day of April, 2024

Katherine Kelly Vidal
*Director of the United States Patent and Trademark Office*